(12) United States Patent
Michalak (10) Patent No.: US 10,111,741 B2
(45) Date of Patent: Oct. 30, 2018

(54) INTRALUMENAL STENT GRAFT FIXATION

(71) Applicant: W. L. Gore & Associates, Inc., Newark, DE (US)

(72) Inventor: Christopher S. Michalak, Elkton, MD (US)

(73) Assignee: W. L. Gore & Associates, Inc., Newark, DE (US)

( * ) Notice: Subject to any disclaimer, the term of this patent is extended or adjusted under 35 U.S.C. 154(b) by 197 days.

(21) Appl. No.: 14/882,853

(22) Filed: Oct. 14, 2015

(65) Prior Publication Data

US 2016/0120638 A1    May 5, 2016

Related U.S. Application Data

(60) Provisional application No. 62/072,115, filed on Oct. 29, 2014.

(51) Int. Cl.
| | | |
|---|---|---|
| *A61F 2/07* | (2013.01) | |
| *A61F 2/848* | (2013.01) | |
| *A61F 2/89* | (2013.01) | |
| *A61F 5/00* | (2006.01) | |
| *A61F 2/82* | (2013.01) | |

(Continued)

(52) U.S. Cl.
CPC .............. *A61F 2/07* (2013.01); *A61F 2/848* (2013.01); *A61F 2/89* (2013.01); *A61F 5/0076* (2013.01); *A61F 5/0079* (2013.01); *A61F 2/82* (2013.01); *A61F 2/852* (2013.01); *A61F 2002/045* (2013.01); *A61F 2002/072* (2013.01); *A61F 2002/075* (2013.01); *A61F 2002/828* (2013.01); *A61F 2002/8483* (2013.01); *A61F 2002/8486* (2013.01); *A61F 2220/0016* (2013.01); *A61F 2220/0075* (2013.01)

(58) Field of Classification Search
CPC .... A61F 2/07; A61F 2/82; A61F 2/848; A61F 2/8483; A61F 2/8486; A61F 2/852; A61F 2/89; A61F 2002/045; A61F 2002/072; A61F 2002/075; A61F 2002/828; A61F 5/0076; A61F 5/0079; A61F 2220/0016; A61F 2220/0075

See application file for complete search history.

(56) References Cited

U.S. PATENT DOCUMENTS

| | | | |
|---|---|---|---|
| 2003/0065385 A1 | 4/2003 | Weadock | |
| 2005/0222668 A1* | 10/2005 | Schaeffer | A61F 2/07 623/1.13 |

(Continued)

*Primary Examiner* — Robert Lynch
(74) *Attorney, Agent, or Firm* — Amy L. Miller (57) ABSTRACT

This document describes intralumenal stent graft devices with integrated anchor members that are selectively deployable in situ. The deployment of the anchor members is also reversible, to thereby facilitate retrieval of the stent graft device. These stent graft devices are well-suited for sealing and repairing defects in a body lumen wall. Such defects can include, but are not limited to, aneurysms and lumen wall openings. In some embodiments, the intralumenal stent graft devices provided herein are well-suited for use in the GI tract including the colon. That is the case because the integrated anchor members provide the stent graft devices with a high level of migration resistance, whereby the stent grafts can remain resiliently located in a desired position within the GI tract despite the peristaltic movements of the GI tract.

8 Claims, 4 Drawing Sheets

(51) Int. Cl.
 *A61F 2/04* (2013.01)
 *A61F 2/852* (2013.01)

(56) References Cited

U.S. PATENT DOCUMENTS

| | | | |
|---|---|---|---|
| 2006/0229704 A1* | 10/2006 | Thistle | A61F 2/064 |
| | | | 623/1.13 |
| 2008/0195226 A1* | 8/2008 | Williams | A61F 2/04 |
| | | | 623/23.67 |
| 2008/0255587 A1 | 10/2008 | Cully et al. | |
| 2009/0270971 A1 | 10/2009 | Xiao et al. | |
| 2013/0018450 A1 | 1/2013 | Hunt | |
| 2015/0313599 A1* | 11/2015 | Johnson | A61B 19/54 |
| | | | 606/191 |

\* cited by examiner

INTRALUMENAL STENT GRAFT FIXATION

FIELD

The present disclosure relates generally to implantable medical devices, and more specifically, to intralumenal stent graft devices with integrated anchor features that are selectively deployable and removable.

BACKGROUND

Stent graft devices can be implanted in patients to treat various medical conditions. For example, stent graft devices are implanted within a patient to treat an aneurysm in a blood vessel. In another example, stent graft devices are implanted within a patient to seal an opening within the wall of a body lumen (e.g., GI tract) or organ. In a further example, stent graft devices are implanted within a patient to treat a body lumen that has a stricture, such that the device opens or enlarges a fluid flow pathway through the body lumen.

The need to remove lesions from the wall of the colon is common and growing worldwide. When polyps become large and invasively encompass more than just the mucosal layers of the colon, a colectomy procedure is often performed whereby the full thickness of the colon wall tissue is removed along with the lesion. This procedure can result in an opening of the colon wall. Such an opening is potentially sealable using a stent graft device. However, stent graft devices for use in the gastrointestinal (GI) tract are challenging to develop in part because of the relatively hostile colon environment that includes peristaltic movements and fecal matter.

SUMMARY

This present disclosure relates to intralumenal stent graft devices with integrated anchor members that are selectively deployable in situ. The deployment of the anchor members is also reversible, thereby facilitating retrieval of the stent graft devices. In some embodiments, these stent graft devices are well-suited for sealing defects in a body lumen wall. Such defects can include, but are not limited to, aneurysms and lumen wall openings. In some embodiments, the intralumenal stent graft devices provided herein are well-suited for use in the gastrointestinal (GI) tract including the colon. The integrated anchor members provide the stent graft devices with a high level of migration resistance, whereby the stent grafts can remain resiliently located in a desired position within the GI tract despite the peristaltic movements of the GI tract.

In one implementation, an implantable stent graft device includes a stent frame comprised of one or more elongate members, a covering material attached to the stent frame, and one or more anchor members extending from the stent frame. The anchor members may reconfigure from a deployed configuration to an undeployed configuration by an eversion of a portion of the stent frame. In some embodiments, the anchor members may each comprise a hook portion with a free end. The hook portion may pivot in response to the eversion of the portion of the stent frame. The implantable stent graft device may optionally further comprise a purse string suture. The purse string suture may be engaged with a portion of the stent frame such that tensioning the purse string suture causes the eversion of the portion of the stent frame. The stent frame may further include a plurality of stent rings, and the anchor members may extend from a single first stent ring. In some embodiments, the single first stent ring may be an end-most stent ring of the plurality of stent rings. Alternatively, the single first stent ring may be an inner stent ring of the plurality of stent rings. In some embodiments, some of the anchor members may extend from a first stent ring and others of the anchor members may extend from a second stent ring. The implantable stent graft device may assume a low-profile configuration when the device is within a delivery sheath, and the device may expand from the low-profile configuration and assume an expanded configuration when the device emerges from the delivery sheath. In some embodiments, at least a portion of the covering material may be modified by one or more chemical or physical processes to enhance particular properties of the covering material. The covering material may be modified to inhibit tissue ingrowth and endothelialization into the covering material.

In another implementation, an implantable stent graft system includes a delivery sheath defining a lumen, and a stent graft device. The stent graft includes a stent frame comprised of one or more elongate members, a covering material attached to the stent frame, and one or more anchor members extending from the stent frame. The anchor members reconfigure from a deployed configuration to an undeployed configuration by an eversion of a portion of the stent frame. The stent graft device is configurable in a delivery configuration for confinement within the lumen. The delivery configuration of the stent graft device comprises a low-profile configuration, and the eversion of the portion of the stent frame. In some embodiments, the system may further include a pusher catheter within the lumen. The pusher catheter may be configured and operable to cause the stent graft device to emerge from the lumen. In some embodiments, the anchor members may each comprise a hook portion with a free end. The hook portions may pivot in response to the eversion of the portion of the stent frame. Optionally, the system may further comprise a purse string suture. The purse string suture may be engaged with the portion of the stent frame such that tensioning the purse string suture causes the eversion of the portion of the stent frame.

In another implementation, a method for implanting a stent graft device within a body lumen includes: navigating a delivery sheath containing the stent graft device to a target deployment site in the body lumen, causing the stent graft device to emerge from the delivery sheath, and deploying the one or more anchor members by un-everting the portion of the stent frame. The stent graft device can be configured with the structure and features described herein. The deploying of the anchor members may cause at least one of the anchors to pierce a wall of the body lumen. The body lumen may comprise a colon. The stent graft device may be implanted in the colon to close an opening in a wall of the colon. The body lumen may comprise a blood vessel. The stent graft device may be implanted in the blood vessel to isolate an aneurysm in a wall of the blood vessel. The method for implanting a stent graft device within a body lumen may further comprise removing the stent graft device from the body lumen by everting the portion of the stent frame to reconfigure the one or more anchor members to the undeployed configuration.

Particular embodiments of the subject matter described in this specification can be implemented to realize one or more of the following advantages. In some embodiments the stent graft devices provided herein can be deployed into a body lumen of a patient using a minimally invasive transcatheter technique. The stent graft devices can seal a defect in a body lumen wall to prevent the contents of the body lumen from exiting the lumen. The sealing function provided by the stent graft devices can promote healing of a body lumen wall defect by isolating the defect from the contents of the body lumen that may otherwise tend to inhibit the healing of the defect. In some embodiments, the stent graft devices provided herein can be used treat aneurysms in blood vessels. The stent graft devices provide resilient fixation and consistent sealing of body lumen wall defects, even when positioned in body lumens that include anatomical movements, such as the peristaltic movements of the GI tract. Further, the stent graft devices are designed so as to not inhibit such movements. In some embodiments, the stent graft devices provided herein can be deployed into a colon to seal a perforation related to a lesion resection. In such circumstances, the stent graft devices facilitate minimally invasive treatment of large colon lesions. In some embodiments, the stent graft devices provided herein are repositionable and retrievable.

BRIEF DESCRIPTION OF THE DRAWINGS

The accompanying drawings are included to provide a further understanding of the disclosure and are incorporated in and constitute a part of this specification, illustrate embodiments of the disclosure, and together with the description, serve to explain the principles of the disclosure.

DETAILED DESCRIPTION

This document describes implantable medical devices. For example, this document provides intralumenal stent graft devices with integrated anchor members that are selectively deployable in situ. The deployment of the anchor members is also reversible. Therefore, stent graft devices that have integrated anchor members as described herein may be retrievable after implantation.

The anchor members described herein provide stent graft devices with a high degree of migration resistance. Stent graft devices with such integrated anchor members are therefore well-suited for use in intralumenal contexts such as, but not limited to, gastrointestinal (GI) tracts and vasculatures. In some implementations, the stent graft devices described herein are implanted in a patient to seal an opening in a body lumen wall. Such openings can be caused by a number of medical situations, such as, for example, a resection to remove a lesion, a burst aneurysm, a trauma-induced hole or tear, a fistula, diseases such as appendicitis or diverticulitis, Crohn's disease, and/or ulcers. In some other implementations, the stent graft devices provided herein are implanted in a patient to isolate an aneurysm, and thereby reduce the risk that the aneurysm will burst. In some other implementations, the stent graft devices provided herein are implanted in a patient in the location of a lumen stricture to create or enlarge an open passageway for fluid flow. It should be understood that the stent graft devices provided herein are scalable to a broad range of sizes so that the stent graft devices can be used in a wide variety of different anatomies, implant sites (e.g., body lumens, organs, cavities, and the like), and types of implementations.

In general, the stent graft devices provided herein can be delivered to, and deployed at, an in vivo deployment site within a body of a patient using various minimally invasive transcatheter deployment techniques. Therefore, in some embodiments the stent graft devices described herein can be configured in two or more configurations. For example, while the stent graft device is being delivered to the deployment site within a delivery sheath, the device may be configured in a collapsed, low-profile delivery configuration within a lumen of the delivery sheath. After emergence of the stent graft device from the delivery sheath, the device may assume an expanded or deployed configuration. In some embodiments, the stent graft device may self-expand to the expanded or deployed configuration. In some embodiments, the stent graft device may expand in response to the application of supplemental force from another device (e.g., a dilation balloon). In some embodiments, a combination of self-expansion and forced expansion may be used to expand the stent graft device.

The stent graft devices provided herein are generally illustrated and/or described in the context of their fully expanded configurations. However, the stent graft devices provided herein tend to expand in conformance to the topography of the surrounding tissue when the devices are implanted within a patient. Therefore, it should be understood that the in situ deployed configuration of the stent graft devices may or may not be the fully expanded configuration of the devices. That is, while the stent graft device is deployed, for example, the device may assume one or more partially expanded or partially deployed configurations.

Figure 1:
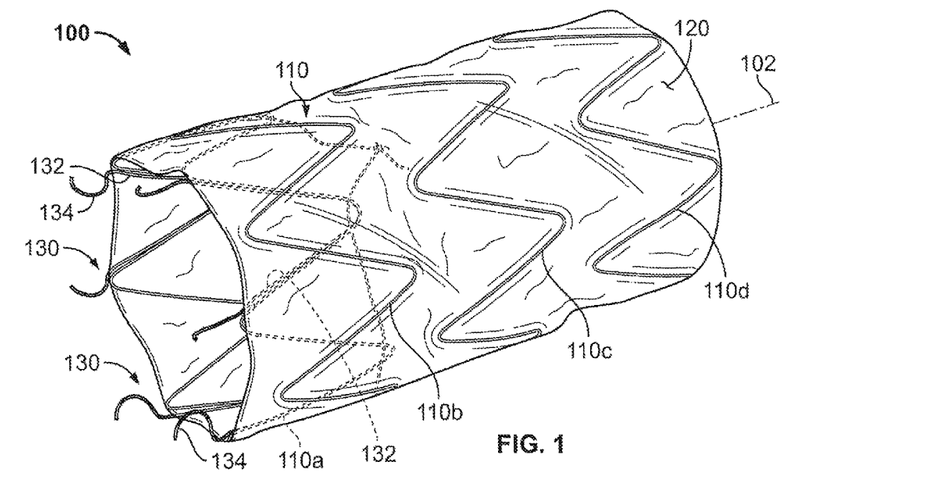
FIG. 1 is a perspective view of an intralumenal stent graft device with integrated selectively deployable anchor members positioned in an undeployed configuration in accordance with at least one embodiment of the invention.

Referring to FIG. 1, an example stent graft device 100 includes a stent frame 110, a covering material 120, and selectively deployable anchor members 130. The stent frame 110 is attached to the covering material 120. The anchor members 130 are attached to the stent frame 110 and to the covering material 120.

As will be described further below, in the depicted configuration shown in FIG. 1, the anchor members 130 are in their undeployed orientation. In this configuration, the anchor members 130 are undeployed because the portion of the stent graft device 100 that includes the anchor members 130 is everted (folded) inside of other portions of the stent graft device 100. As will be described further below, the act of unfolding (un-everting) the portion of the stent graft device 100 that includes the anchor members 130 deploys the anchor members 130 so that the stent graft device 100 can become anchored to the surrounding tissue.

In the depicted embodiment of FIG. 1, the stent graft device 100 is generally cylindrical and defines a longitudinal axis 102. In some embodiments, the stent graft device 100 is diametrically tapered. Additionally, the stent graft device 100 may have one or more portions that are larger in diameter than one or more other portions of the stent graft device 100. In at least one embodiment, the stent graft device 100 has one or more flared ends. The ends of the stent graft device 100 may be scalloped or contoured to the shape of the stent frame. Additionally, one or more fenestrations may be included in the stent graft device 100. In some embodiments, one or more side branches may be included in the stent graft device 100. The covering material 120 may also include one or more folds, pleated portions, gathered portions, accordion-folded portions, and/or the like, and combinations thereof.

The stent frame 110 can be comprised of various materials and combinations of materials. In some embodiments, nitinol (NiTi) is used as the material of the stent frame 110, but other materials such as stainless steel, L605 steel, polymers, MP35N steel, stainless steels, polymeric materials, a cobolt, chromium, nickel alloy (e.g., Pyhnox or Elgiloy), or any other appropriate biocompatible material, and combinations thereof can be used as the material of the stent frame 110. In some embodiments, bioresorbable or bioabsorbable materials may be used, including for example, a bioresorbable or bioabsorbable polymer. The super-elastic properties of NiTi make it a particularly good candidate material for the stent frame 110 because, for example, NiTi can be heat-set into a desired shape. That is, NiTi can be heat-set so that the stent frame 110 tends to self-expand into a desired shape when the stent frame 110 is unconstrained, such as when the stent frame 110 is deployed out from a delivery sheath. A stent frame 110 made of NiTi, for example, may have a spring nature that allows the stent frame 110 to be elastically collapsed or "crushed" to a low-profile delivery configuration and then to reconfigure to the expanded configuration as shown in FIG. 1. The stent frame 110 may be generally conformable, fatigue resistant, and elastic such that the stent frame 110 can conform to the topography of the surrounding tissue when the stent graft device 100 is deployed in a patient.

In some embodiments, the stent graft device 100 includes features for enhanced radiographic visibility. In some embodiments, some or all portions of the stent frame 110 (and the stent frames of the other devices provided herein) are coated (e.g., sputter coated) with a radiopaque coating. For example, in some such embodiments portions or all of the stent frame 110 can be coated with a noble metal such as, but not limited to, tantalum, platinum, and the like. In some embodiments, one or more radiopaque markers are attached to the stent frame 110, or to the covering material 120, or to both the stent frame 110 and the covering material 120. In some embodiments, drawn tubular wires such as NiTi wires containing platinum, tantalum, iridium, palladium, or the like, can be used.

In the depicted embodiment, the stent frame 110 comprises four discrete annular stent rings: a first stent ring 110a, a second stent ring 110b, a third stent ring 110c, and a fourth stent ring 110d. The stent rings 110a, 110b, 110c, and 110d are spaced apart from each other and independent of each other. In the depicted embodiment, each stent ring 110a, 110b, 110c, and 110d comprises a wire loop that is shaped into a generally sinusoidal waveform. As such, the stent rings 110a, 110b, 110c, and 110d have multiple apices that are interconnected by generally linear portions. In some embodiments, the stent rings 110a, 110b, 110c, and 110d are heat-set into the generally sinusoidal waveform. However, it should be understood that the depicted stent frame 110 is not the only stent frame configuration envisioned within the scope of this disclosure. Rather, the stent frame 110 can differ from the depicted configuration in numerous ways such as, but not limited to, the number of stent rings, the shape of the stent rings, the diameter of the stent rings, the diameter of the wire (also referred to herein as elongate members), and the like.

In some embodiments, some or all of the stent frame 110 is comprised of a framework construct that differs from the stent rings as depicted. For example, in some embodiments some or all of the stent frame 110 is a single helically wound elongate member. In some embodiments, some or all of the stent frame 110 comprises stent rings that have interconnecting elements. In some embodiments, some or all of the stent frame 110 is comprised of braided or interwoven elongate members. In some embodiments, some or all of the stent frame 110 comprises a cellular construct. In some embodiments, some or all of the stent frame 110 comprises a combination of such constructs and/or other types of stent framework constructs.

In some embodiments, the width and/or thickness of the elongate members of the stent frame 110 may be within a range of about 0.008" to about 0.015" (about 0.20 mm to about 0.40 mm), or about 0.009" to about 0.030" (about 0.23 mm to about 0.76 mm), or about 0.01" to about 0.06" (about 0.25 mm to about 1.52 mm), or about 0.02" to about 0.10" (about 0.51 mm to about 2.54 mm). In some embodiments, the elongate members of the stent frame 110 may have smaller or larger widths and/or thicknesses. In some embodiments, each of the elongate members of the stent frame 110 has essentially the same width and/or thickness. In some embodiments, one or more of the elongate members of the stent frame 110 has a different width and/or thickness than one or more of the other elongate members of the stent frame 110. In some embodiments, one or more portions of one or more of the elongate members of the stent frame 110 may be tapered, widened, narrowed, curved, radiused, wavy, spiraled, angled, and/or otherwise non-linear and/or not consistent along the entire length of the elongate members of the stent frame 110. Such features and techniques can also be incorporated with any other embodiment of the stent graft provided herein.

In some embodiments, the elongate members of the stent frame 110 may be of a single diameter, thickness and/or width through the entirety of the stent frame 110. In some embodiments, the elongate members of the stent frame 110 may vary in diameter, thickness and/or width so as to facilitate variations in the radial force that is exerted by the stent frame 110 in specific regions thereof, to increase or decrease the flexibility of the stent frame 110 in certain regions, to enhance migration resistance, and/or to control the process of compression (crushability) in preparation for deployment and the process of expansion during deployment of the stent graft device 100.

In some embodiments, the elongate members of the stent frame 110 may have a circular cross-section. In some embodiments, the elongate members of the stent frame 110 may have a rectangular cross-sectional shape, or another cross-sectional shape that is not rectangular. Examples of cross-sectional shapes that the elongate members stent graft 110 may have include, but are not limited to, circular, square, ovular, rectangular, elliptical, triangular, O-shaped, trapezoidal, including irregular cross-sectional shapes formed by a braided or stranded construct. In some embodiments, the elongate members of the stent frame 110 may be essentially flat (i.e., such that the width to thickness ratio is about 2.1, about 3:1, about 4:1, about 5:1, or greater than about 5:1). In some examples, the elongate members of the stent frame 110 may be formed using a center-less grind technique, such that the diameter of the elongate members varies along the length of the elongate members.

In some embodiments, the stent frame 110 is a combination of two or more dissimilar elongate members having differing cross-sectional shapes and/or sizes (e.g., thickness, width, diameter, etc.). To provide one such example, in some embodiments some of the elongate members at a particular location on the stent frame 110 have larger diameters than some of the elongate members at other locations on the same stent frame 110. In addition, the elongate members forming the anchor members 130 may have a different size, cross-sectional shape, and/or material than some or all of the elongate members of the stent frame 110.

While the stent frame 110 has thus far been generally described as comprising wire elongate members that are wound or otherwise formed so as to attain a desired configuration, in some embodiments the elongate members of the stent frame 110 are formed from a tube or sheet of a material that is cut according to a pattern and then expanded (and in some embodiments heat-set). For example, the elongate members of the stent frame 110 may be fashioned from a tubular material to form rings and/or cellular structures. In some embodiments, the elongate members of the stent frame 110 are cut from a sheet of material that is then formed into a ring or tubular cellular structure. Such cutting may be performed by laser cutting, chemical etching, machining, water-jet cutting. The anchor members 130 may be integrally formed with the stent frame 110. Such integrally formed anchor members 130 can be cut into their final shape and configuration, or such anchor members 130 can be formed into their final shape and configuration after cutting.

Still referring to FIG. 1, the stent frame 110 provides structure and shape for the stent graft device 100 in general. In the depicted embodiment, the covering material 120 is attached to the scaffold of the stent frame 110 to create a tubular fluid conduit. The stent frame 110 thereby provides a supportive structural framework for the covering material 120 that may otherwise be relatively flaccid and flexible. Flexibility of the covering material 120 allows the portion of the stent graft device 100 that includes the anchor members 130 to be everted inside of the other portions of the stent graft device 100, and to be un-averted (unfolded) for deployment of the anchor members 130.

In the depicted embodiment of FIG. 1, the covering material 120 is disposed essentially on the entire stent frame 110. As used herein, the term 'essentially on' is meant to denote that the covering is disposed entirely over the frame 110 or nearly covering the frame 110. In some embodiments, the covering material 120 is disposed on one or more portions of the stent frame 110, while one or more other portions of the stent frame 110 do not have the covering material 120 disposed thereon. While the depicted embodiment includes the covering material 120, the covering material 120 is not required in all embodiments. In some embodiments, two or more portions of covering material 120, which can be separated and/or distinct from each other, can be disposed on the stent frame 110. That is, in some embodiments, a particular type of covering material 120 is disposed on some areas of the stent frame 110 and a different type of covering material 120 is disposed on other areas of the stent frame 110. Such features and techniques can also be incorporated with other embodiments of the stent graft devices provided herein.

The covering material 120 is disposed on the inside and the outside of the stent frame 110 in FIG. 1. In some embodiments, the covering material 120 is disposed on the just the outside of the stent frame 110. In some embodiments, the covering material 120 is disposed on the just the inside of the stent frame 110. In some embodiments, some portions of the stent frame 110 are covered by the covering material 120 in a different manner than other portions of the stent frame 110.

The covering material 120 is attached to at least some portions of the stent frame 110. In some embodiments, the covering material 120 is attached to at least some portions of the stent frame 110 using an adhesive. In some embodiments, FEP (fluorinated ethylene propylene) is used as an adhesive to attach the covering material 120 to the stent frame 110, or portions thereof. For example, an FEP coating can be applied to some or all portions of the stent frame 110, and the FEP acts as a bonding agent to adhere the covering material 120 to the stent frame 110. In some embodiments, a radiopaque material can be combined with the adhesive that is used to attach the covering material 120 to the stent frame 110. For example, a radiopaque powder (e.g., tungsten powder) could be mixed with the adhesive. When such a radiopaque material is used in conjunction with the adhesive for attaching the covering material 120 to the stent frame 110, the stent frame device 100 (and other devices described herein that include such radiopaque material) can be enhanced from a radiographic visualization standpoint (e.g., using fluoroscopy). In some embodiments, stitching, lashing, banding, and/or clips, and the like can be used to attach the covering material 120 to the stent frame 110. In some embodiments, portions of the covering material 120 are disposed on the inside and on the outside of the stent frame 110 and the portions of the covering material 120 are adhered to each other so as to encapsulate portions of the stent frame 110. In some embodiments, a combination of techniques are used to attach the covering material 120 to the stent frame 110. Such features and techniques can also be incorporated with other embodiments of stent graft devices provided herein.

In some embodiments, the covering material 120 is made of a membranous material that inhibits or reduces the passage of blood, bile, and other bodily fluids and materials through the covering material 120. In some embodiments, the covering material 120, or portions thereof, has a material composition and/or configuration that inhibits or prevents tissue ingrowth and/or endothelialization to the covering material 120. In some embodiments, the covering material 120, or portions thereof, has a microporous structure that provides a tissue ingrowth scaffold for durable sealing and/or supplemental anchoring strength of the sealing device.

The covering material 120 may include a fluoropolymer, such as an expanded polytetrafluoroethylene (ePTFE). In some embodiments, the covering material 120 comprises a polyester, a silicone, a urethane, another biocompatible polymer, DACRON® (polyester), bioadsorbable systems, copolymers, or combinations and subcombinations thereof. In some embodiments, the covering material 120 is manufactured using techniques such as, but not limited to, extrusion, expansion, heat-treating, sintering, knitting, weaving, chemically treating, and the like.

In some embodiments, the covering material 120 is configured such that the modulation of fluid passage through the covering material 120 is immediate and does not rely on a thrombotic process. The covering material 120 can be modified by one or more chemical or physical processes that enhance certain physical properties of the covering material 120. For example, a hydrophilic coating may be applied to the covering material 120 to improve the wettability and echo translucency of the covering material 120. In some embodiments, the covering material 120 may be modified with chemical moieties that promote or inhibit one or more of endothelial cell attachment, endothelial cell migration, endothelial cell proliferation, and resistance to thrombosis. Additionally, the covering material 120 may be modified with covalently attached heparin or impregnated with one or more drug substances that are released in situ to promote wound healing or reduce tissue inflammation. In one or more embodiments, the drug may be a corticosteroid, a human growth factor, an anti-mitotic agent, an antithrombotic agent, or dexamethasone sodium phosphate.

In some embodiments, the covering material 120 is pre-perforated to modulate fluid flow through the covering material 120, to create filtering properties, and/or to affect the propensity for tissue ingrowth to the covering material 120. In some embodiments, the covering material 120 is treated to make the covering material 120 stiffer or to add surface texture. For example, in some embodiments the covering material 120 is treated with FEP powder to provide a stiffened covering material 120 or roughened surface on the covering material 120. In some embodiments, selected portions of the covering material 120 are treated, while other portions of the covering material 120 are not treated. Other covering material 120 treatment techniques can also be employed to provide beneficial mechanical properties and tissue response interactions. Such materials and techniques can be used for any of the stent graft devices provided herein. In some embodiments, portions of the covering material 120 have one or more radiopaque markers attached thereto to enhance in vivo radiographic visualization.

As will be described in more detail below, in some implementations the stent graft device 100 is configured to be implanted in a patient such that the covering material 120 overlays and seals an opening in a body lumen wall. In that manner, the stent graft device 100 beneficially restricts the transfer of biomaterials through the opening, and also promotes healing of the opening by isolating the opening from the contents of the body lumen that otherwise may tend to inhibit the healing process of the tissue surrounding the opening. In some implementations, the stent graft device 100 is configured to be implanted in a patient such that the covering material 120 overlays and isolates an aneurysm or weakened portion of a body lumen wall. Such isolation of an aneurysm or weakened portion of a body lumen wall may thereby serve to prevent a burst of the body lumen.

Still referring to FIG. 1, the selectively deployable anchor members 130 are attached to the first stent ring 110a. In some embodiments, anchor members 130 are attached to other stent rings or other portions of the stent frame 110. While in the depicted embodiment anchor members 130 are attached only to the first stent ring 110a, in some embodiments two or more sets of anchor members 130 are included in a single stent graft device 100. For example, in some embodiments anchor members 130 are attached to the first stent ring 110a and the fourth stent ring 110d. In that fashion, both ends of the stent graft device 100 can be positively anchored to the surrounding tissue. Additionally or alternatively, in some embodiments one or more other stent rings (e.g., stent rings 110b and/or 110c) can have anchor members 130 attached thereto. It should be understood that the placement of the anchor members 130 can be widely varied in various embodiments of the stent graft devices provided herein.

The anchor members 130 may include stent attachment portions 132 (refer to FIG. 2) and hook portions 134. In some embodiments, the anchor members 130 are integrally formed with the stent frame 110 and therefore include just the hook portions 134. The anchor members 130 can include elongate members having any of the materials and characteristics of the elongate members of the stent frame 110 as described above.

In the depicted embodiment of FIG. 1, the stent attachment portions 132 are attached to the first stent ring 110a. The attachment of the stent attachment portions 132 to the first stent ring 110a can be performed by various techniques such as, but not limited to, welding, gluing, using a collar, using shrink tubing, twisting, braiding, sheathing, lashing, and the like, and combinations thereof. Any suitable manner by which the anchor members 130 can be attached to the stent frame 110 is within the scope of this disclosure.

The anchor members 130 may also include the hook portions 134. The hook portions 134 extend from the first stent ring 110a in a cantilever arrangement. While in the depicted embodiment there are six hook portions 134, fewer or more than six hook portions 134 may be included. For example, one, two, three, four, five, seven, eight, nine, ten, eleven, twelve, or more than twelve hook portions 134 may be included in a single stent graft. While in the depicted embodiment a hook portion 134 extends from every second apex of the waveform defined by the first stent ring 110a, other arrangements may be used. That is, in some embodiments some apices may have a hook portion 134 extending therefrom while other apices may not have a hook portion 134 extending therefrom. All such possible arrangements are within the scope of this disclosure.

In some embodiments, the hook portions 134 each comprise a curved elongate member that terminates at a free end that is configured to puncture tissue during the deployment process (as described further below). In some embodiments, the curved portions of the hook portions 134 are generally semicircular, i.e., the curved portions define an arc of about 180°. In some embodiments, the curved portions of the hook portions 134 define an arc in a range from about 45° to about 75°, or about 60° to about 90°, or about 75° to about 105°, or about 90° to about 120°, or about 105° to about 135°, or about 120° to about 150°, or about 135° to about 165°, or about 150° to about 180°, or about 165° to about 195°, or about 180° to about 210°, or about 195° to about 225°, or about 210° to about 240°, or greater than about 240°. In the undeployed configuration of FIG. 1, the hook portions 134 free ends of the anchor members 130 are oriented such that the free ends of the hook portions 134 are pointing generally radially outward from the longitudinal axis 102. In that orientation, the anchor members 130 are positioned to be able to puncture lumen wall tissue as the anchor members 130 are pivoted during the deployment process. In some embodiments, the free ends of the hook portions 134 are sharpened to facilitate tissue penetration.

In some embodiments, some features are included in the anchor members 130 (or other portions of the stent graft device 100) to enhance the anchorage strength and migration resistance of the stent graft device 100 in relation to the surrounding tissue. Such features may facilitate improved stent graft device 100 performance by allowing the device to provide a reliably durable seal with the surrounding tissue, by causing the device to resist in situ migration, for example. For example, in some embodiments the anchor members 130 include features directed to enhancing migration resistance such as, but not limited to, macro anchor features (e.g., prongs, hooks, barbs, atraumatic probes, spikes, etc.), micro anchor features (e.g., a grouping of small protrusions, surface texturing, etc.), features that facilitate tissue ingrowth and/or endothelialization, and the like, and combinations thereof. In some embodiments, other types of anchor features may be located on other portions of the stent graft device 100.

Figure 2:
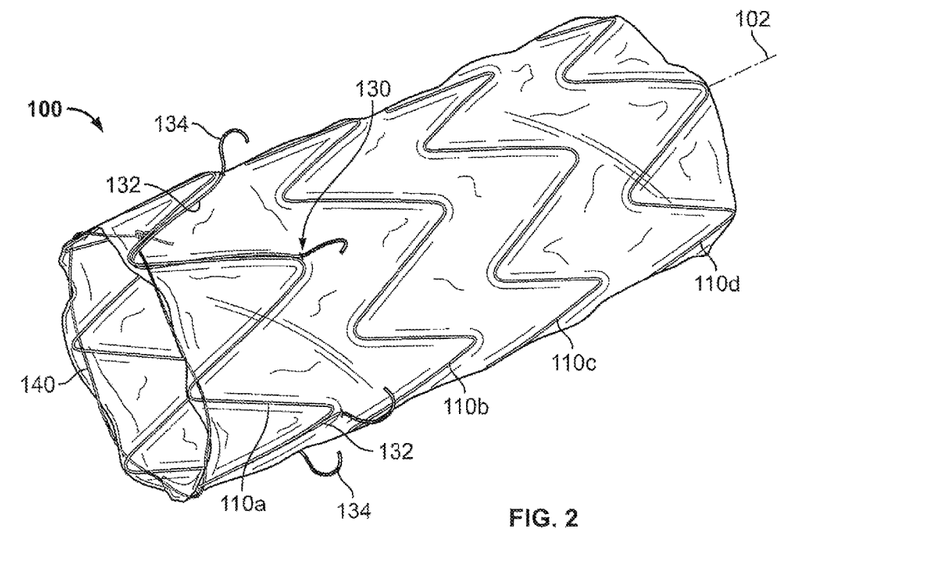
FIG. 2 is a perspective view of the stent graft device of FIG. 1 showing the anchor members in a deployed configuration in accordance with one embodiment of the invention.

Referring now to FIG. 2, the stent graft device 100 is shown with the anchor members 130 in the deployed configuration. In this configuration, the anchor members 130 are deployed because the portion of the stent graft device 100 that includes the anchor members 130 is un-everted (unfolded) from being everted inside of the other portions of the stent graft device 100 (as depicted in FIG. 1). The act of unfolding the portion of the stent graft device 100 that includes the anchor members 130, deploys the anchor members 130 so that the stent graft device 100 can become anchored to the surrounding tissue.

In the deployed configuration, the hook portions 134 of the anchor members 130 are located outside of the cylindrical profile defined by the covering material 120, and the free ends of the hook portions 134 are pointing generally radially inward. In that orientation, the anchor members 130 are oriented in a deployed configuration that can engage with the wall of a body lumen in which the stent graft 100 is deployed.

Figure 3:
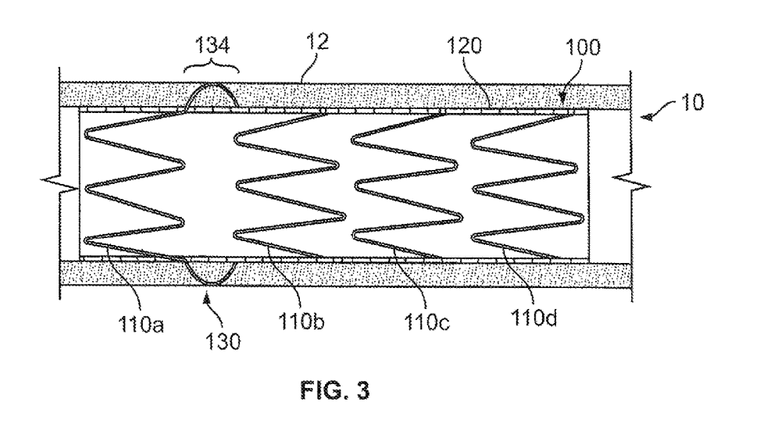
FIG. 3 is a cross-sectional view of the stent graft device of FIG. 1 within a body lumen with the anchor members deployed in engagement with a body lumen wall according to at least one embodiment of the invention.

Referring now to FIG. 3, the stent graft device 100 is depicted as deployed within a body lumen 10 that has a lumen wall 12. The stent graft device 100 is shown with the anchor members 130 in their deployed configuration (corresponding to the configuration shown in FIG. 2). The body lumen 10 and stent graft device 100 are shown in longitudinal cross-section so that the engagement of the anchor members 130 with the lumen wall 12 can be visualized. It is envisioned in some embodiments that the anchor members 130 provide strong migration resistance for the stent graft device 100. That is the case even in the context of the GI tract with its peristaltic motions that propel the GI tract contents, e.g., from the small intestines to the large intestines (including the colon).

When the anchor members 130 are in the deployed configuration, the hook portions 134 of the anchor members 130 are at least partially engaged with the lumen wall 12. In some embodiments, the entirety of the curved hook portions 134 are located within the lumen wall 12. In some embodiments, a portion of one or more of the hook portions 134 are exposed on the outside of the lumen 10. In some embodiments, the free ends (tips) of the hook portions 134 are all within the lumen wall 12. In other embodiments, the free end (tip) of one or more of the hook portions 134 protrude through the inner wall of the lumen 12. In some such embodiments, the free end (tip) of one or more of the hook portions 134 touches the covering material 120. In some such embodiments, the free end (tip) of one or more of the hook portions 134 punctures the covering material 120. In some embodiments, the hook portions 134 are coated with a coating that inhibits thrombus formation.

Figure 4:
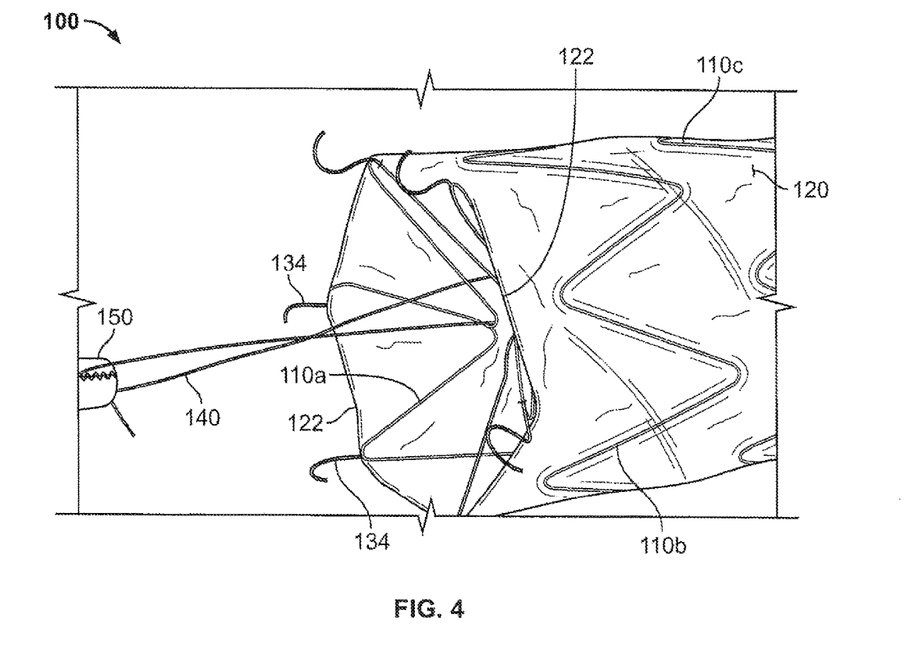
FIG. 4 is a perspective view of an end portion of the stent graft device of FIG. 1 with the anchor members in a first state of partial deployment in accordance with one embodiment of the invention.
Figure 5:
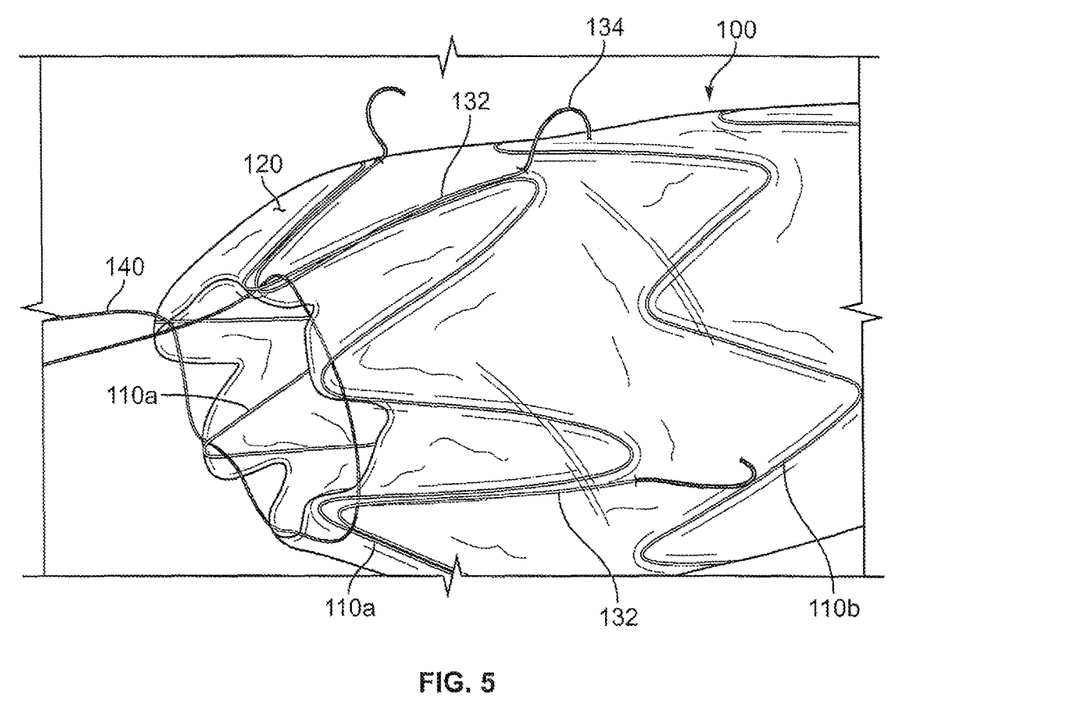
FIG. 5 is a perspective view of an end portion of the stent graft device of FIG. 1 with the anchor members in a second state of partial deployment according to at least one embodiment of the invention.

Referring to FIGS. 4 and 5, an end portion of the stent graft device 100 (approximately 6 of the stent graft device 100) is shown with the anchor members 130 in different stages of deployment. In FIG. 4, the deployment process is just beginning, and in FIG. 5 the deployment process is nearing its end. In FIG. 4, the anchor members 130 are undeployed because the portion of the stent graft device 100 that includes the anchor members 130 is everted (folded) inside of the other portions of the stent graft device 100. The act of unfolding the portion of the stent graft device 100 that includes the anchor members 130 deploys the anchor members 130 (as depicted in FIG. 5) so that the stent graft device 100 can become anchored to the surrounding tissue.

In some embodiments, the stent graft device 100 includes a purse string suture 140. In the depicted embodiment, the purse string suture 140 is passed through some apices of the stent ring 110a. The purse string suture 140 provides a convenient way for a clinician operator to unfold (un-evert) the portion of the stent graft device 100 that includes the anchor members 130. For example, a grasping device 150 (or another tool) can be used to pull on the purse string suture 140 and to thereby unfold (un-evert) the portion of the stent graft device 100 that includes the anchor members 130. In addition, the purse string suture 140 may provide a convenient way for a clinician operator to evert the portion of the stent graft device 100 that includes the anchor members 130 when retrieval of the stent graft device 100 is desired. Doing so can reverse the engagement of the anchor members 130 with the lumen wall. That is, during retrieval of the stent graft device 100, tensioning the purse string suture 140 can cause the anchor members 130 to disengage from the lumen wall, and thereafter the stent graft device 100 can be removed from the patient.

In some embodiments, the purse string suture 140 can be slidably coupled with the stent frame 110 at various locations on the stent frame 110. In some such locations on the stent frame 110, eyelets, bends, apices, loops, and the like, can be used to facilitate the coupling between the stent frame 110 and the purse string suture 140. In some embodiments, the purse string suture 140 can be remain coupled to the stent frame 110 when the stent graft device 100 is in use in a body lumen. In some embodiments, the purse string suture 140 can be removed from the stent frame 110 when the stent graft device 100 is in use in a body lumen. In some embodiments, the purse string suture 140 can be made of a polymer material including, but not limited to, nylon, polypropylene, polytetrafluoroethylene (PTFE), silk, and the like. In some embodiments, the purse string suture 140 can be made of a metallic material including, but not limited to, nitinol, aluminum, stainless steel, and the like. The purse string suture 140 can be a monofilament, a braided multifilament, and the like.

As best seen in FIG. 4, the covering material 120 of the stent graft device 100 (when in the everted configuration as shown) defines a circumferential fold line 122. The circumferential fold line 122 generally corresponds to the location of the apices of the first stent ring 110a from which the hook portions 134 extend. The circumferential fold line 122 acts as a hinge point, pivot point, or fulcrum as the anchor members 130 are deployed and/or undeployed by the manipulation of the purse string suture 140.

With the circumferential fold line 122 acting as the fulcrum, the first stent ring 110a acts as a lever when the purse string suture 140 is pulled (tensioned) by an operator using a tool such as the grasping device 150. With the tension on the purse string suture 140 providing the effort force, the hook portions 134 can exert a load force as the anchor members 130 pivot about the fulcrum (i.e., the circumferential fold line 122). The load force associated with the hook portions 134 can cause the free ends of the hook portions 134 to puncture and penetrate the tissue surrounding the stent graft device 100. In this fashion, the anchor members 130 can be deployed to engage with surrounding tissue such as a lumen wall. In some implementations, the operator may use the grasping device 150 (or another tool) to push the first stent ring 110a fully open such that it is generally parallel to the lumen.

When retrieval of the stent graft device 100 from the body lumen is desired, a grasping device 150 can be routed to the location of the stent graft device 100 in the patient's body. The grasping device 150 can be used to couple with the purse string suture 140 and to evert the portion of the stent graft device 100 that includes the anchor members 130 so that the hook portions 134 become disengaged from surrounding tissue.

Various techniques can be used by the operator to evert the portion of the stent graft device 100 that includes the anchor members 130 so that the hook portions 134 become disengaged from surrounding tissue. In one example, the operator can engage the grasping device 150 with the purse string suture 140 (in the orientation depicted in FIG. 4), and then push the gasping device 150 towards the interior of the stent graft device 100. That action can evert the portion of the stent graft device 100 that includes the anchor members 130 so that the hook portions 134 become disengaged from surrounding tissue. In another example, the operator can approach the stent graft device 100 with the grasping device 150 from the other end of the stent graft device 100. The grasping device 150 can be positioned within the interior of the stent graft device 100 and the grasping device 150 can engage the purse string suture 140. Then the operator can pull on the grasping device 150, which results in eversion of the portion of the stent graft device 100 that includes the anchor members 130 so that the hook portions 134 become disengaged from surrounding tissue.

In some embodiments, the stent graft device 100 can be pulled into a retrieval sheath (not shown) once the hook portions 134 have become disengaged from the surrounding tissue. In some embodiments, a funnel (not shown) can be included on the distal end of the retrieval sheath. Such a funnel provides a wider initial opening at the distal tip of the retrieval sheath to facilitate the capture of all portions of the stent graft device 100. As the grasping device 150 is further retracted, the entire stent graft device 100 can be pulled into the lumen of the retrieval sheath. Then the retrieval sheath containing the stent graft device 100 can be removed from the patient.

Figure 6:
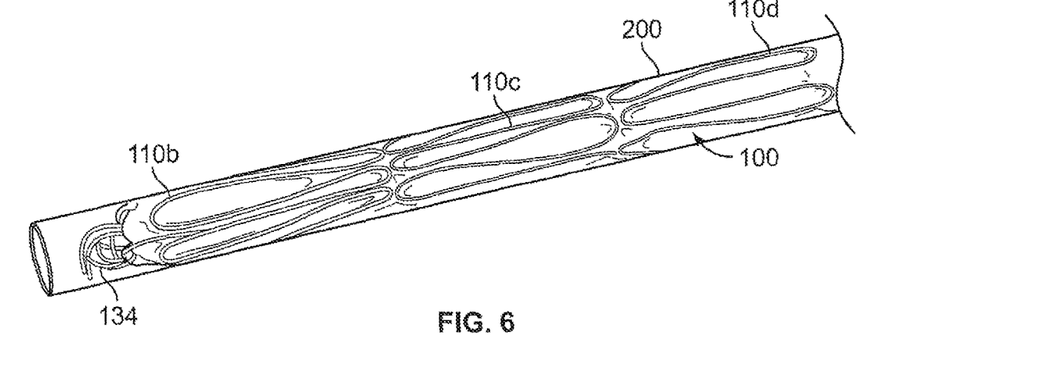
FIG. 6 is a perspective view of the stent graft device of FIG. 1 contained in a delivery sheath according to one or more embodiment of the invention.

Referring to FIG. 6, as described above, the stent graft device 100 is sufficiently flexible to be configured into a low-profile delivery configuration for containment within a deliver/sheath 200. The anchor members 130 on the stent graft devices provided herein are also designed to be flexible and resilient such that the anchor members 130 can be folded to a low-profile delivery configuration for containment within the delivery sheath 200, and can be translated within the delivery sheath 200 without significant dragging resistance. When deployed from the delivery sheath 200, the anchor members 130 revert to a curved or other intended configuration (e.g., as shown in the Figures provided, or similar to as shown). Thereafter, the portion of the stent graft device 100 that is everted, and that includes the anchor members 130, can be un-everted (unfolded) to engage the anchor members 130 with the tissue surrounding the stent graft device 100 at the deployment site.

When the stent graft device 100 is contained within the delivery sheath 200 in the low-profile delivery configuration, at least the portion of the stent graft device 100 that includes the selectively deployable anchor members 130 is everted. To deploy the stent graft device 100, in some implementations the delivery sheath 200 is introduced to a lumen of the patient through a natural body orifice of the patient. In some implementations, the delivery sheath 200 is percutaneously introduced into the patient and advanced within the patient (e.g., through the vasculature), until a distal end of the delivery sheath 200 is located at or near the target in viva deployment site. Various imaging modalities (e.g., fluoroscopy) may be used to facilitate guidance and placement of the devices.

In some embodiments, a pusher catheter (not shown) is within the delivery sheath 200. The pusher catheter may be releasably coupled to the stent graft device 100. In some embodiments, the pusher catheter is not engaged with the stent graft device 100 other than being configured to push the stent graft device 100 while the stent graft device 100 is within the delivery sheath 200. The pusher catheter can be manipulated by an operator to cause the stent graft device 100 to emerge from the delivery sheath 200 at a target location within a patient. In some embodiments, as the stent graft device 100 emerges from the delivery sheath 100, the stent graft device 100 will self-expand and generally conform to the topography of the surrounding tissue (e.g., the lumen wall). In some embodiments, supplemental force (such as from a dilation balloon) can be applied to cause the stent graft device 100 to expand. Initially, after the stent graft device 100 has expanded, the portion of the stent graft device 100 that was everted while in the delivery sheath 200 remains everted in situ. Thereafter, an operator can use a tool (such as the grasping device 150) to manipulate the purse string suture 140 (refer to FIGS. 4 and 5). Such manipulation, as described above, can cause the portion of the stent graft device 100 that was everted to become un-everted and cause deployment of the anchor members 130 so that the stent graft device 100 becomes anchored to the surrounding tissue.

Figure 7:
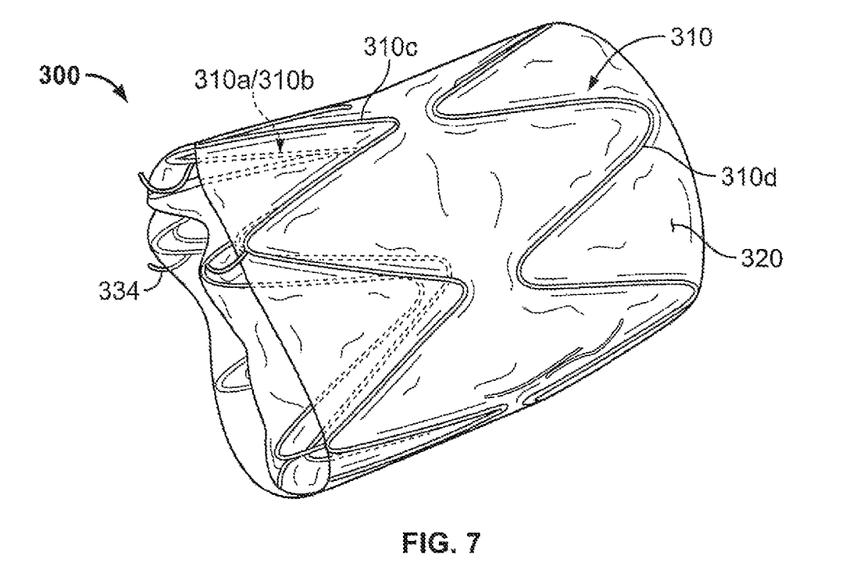
FIG. 7 is a perspective view of an intralumenal stent graft device with integrated selectively deployable anchor members in an undeployed configuration in accordance with at least one embodiment of the invention.
Figure 8:
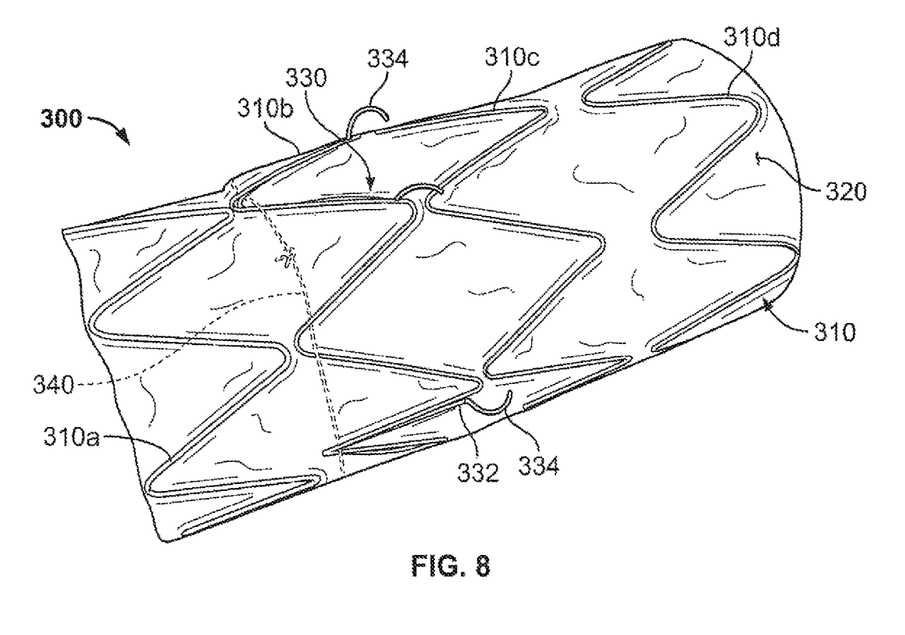
FIG. 8 is a perspective view of the stent graft device of FIG. 7 with the anchor members in a deployed configuration according to at least one embodiment of the invention.

Referring to FIGS. 7 and 8, another example stent graft device 300 with selectively deployable anchor members 330 is illustrated in an undeployed configuration (FIG. 7) and a deployed configuration (FIG. 8). The stent graft device 300 includes a stent frame 310, a covering material 320, and the selectively deployable anchor members 330. The stent frame 310 is attached to the covering material 320. The anchor members 330 are attached to the stent frame 310 and to the covering material 320.

The stent frame 310 in the depicted embodiment comprises four discrete annular stent rings: a first stent ring 310a, a second stent ring 310b, a third stent ring 310c, and a fourth stent ring 310d. As with the stent rings of the stent graft device 100 described above, the stent rings 310a, 310b, 310c, and 310d are spaced apart from each other and independent of each other. It should be understood that the stent frame 310 can include any of the features, additions, or variations described above in reference to the stent frame 110 of stent graft device 100.

The stent graft device 300 includes the covering material 320. It should be understood that the covering material 320 can include any of the features, additions, or variations described above in reference to the covering material 120 of stent graft device 100.

The stent graft device 300 includes a purse string suture 340. It should be understood that the purse string suture 340 can include any of the features, additions, or variations described above in reference to the purse string suture 140 of stent graft device 100.

In the depicted embodiment, the anchor members 330 are attached to a mid-body portion of the stent frame 310. In particular, the anchor members 330 are attached to the second stent ring 310b. In some embodiments, the anchor members 330 are, alternatively or additionally, attached to any one or more of the other stent rings 310a, 310c, or 310d.

As with the stent graft device 100 described above, the stent graft device 300 can be configured such that the anchor members 330 are undeployed. The anchor members 330 may include stent attachment portions 332 (refer to FIG. 8) and hook portions 334. To do so, the portion of the stent graft device 300 that includes the anchor members 330 is everted (as shown in FIG. 7). Since the portion of the stent graft device 300 that includes the anchor members 330 corresponds to the second stent ring 310b, the eversion causes the portion of the stent graft device 300 that includes the first stent ring 310a to be positioned within the everted second stent ring 310b (as shown in FIG. 7). As a result, when the stent graft device 300 is configured such that the anchor members 330 are in the undeployed configuration, the length of the stent graft device 300 is about ½ of the length of the stent graft device 300 when the anchor members 320 are in the deployed configuration (FIG. 8).

The deployment process of the anchor members 320 can take place generally using the same procedure as described above in reference to the deployment of the stent graft device 100. Namely, the stent graft device 300 in the undeployed configuration (i.e., everted as shown in FIG. 7) can be crushed to a low-profile delivery configuration for containment within a delivery sheath. The delivery sheath containing the stent graft device 300 can be navigated within a patient to a target deployment site. Then the stent graft device 300 can be caused to emerge from the delivery sheath. The stent graft device 300 can then expand or be expanded to generally conform to the size and topography of the surrounding tissue. Then, using a tool such as a grasping device, the clinician operator can manipulate the purse string suture 340 so as to un-evert the stent graft device 300. In doing so, the anchor members 330 pivot and the hook portions 334 pierce and penetrate into the surrounding tissue (e.g., lumen wall) to provide positive anchorage for the stent graft device 300. The stent graft device 300 can be retrieved from the deployed location by generally reversing the same sequence of actions, including by everting the portion of the stent graft device 300 that includes the anchor members 302.

Persons skilled in the art will readily appreciate that various aspects of the present disclosure can be realized by any number of methods and apparatus configured to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

What is claimed is:

1. An implantable stent graft device comprising:
    a stent frame including a first annular stent ring, a second annular stent ring, a third annular stent ring, and a fourth annular stent ring;
    a covering material covering the stent frame and forming a cylindrical profile; and
    one or more anchor members extending from apices of the second annular stent ring, said anchor members each having a hook portion with a free end;
    wherein in an un-deployed configuration the first annular stent ring is positioned within an everted second annular stent ring, and
    wherein in a deployed configuration the one or more anchor members are located outside the cylindrical profile defined by the covering material at a mid-body portion of the stent frame.

2. The device of claim 1, wherein in the deployed configuration the free ends of the hook portions point radially inward.

3. The device of claim 1, further comprising a purse string suture, the purse string suture being engaged with the second annular stent ring such that tensioning the purse string suture causes the eversion of the first and second annular stent rings.

4. The device of claim 1, wherein in the un-deployed configuration the stent graft device has a length that is about one half a length of the stent graft device in the deployed configuration.

5. The device of claim 1, wherein at least a portion of the covering material is modified by one or more chemical or physical processes.

6. The device of claim 5, wherein the covering material is modified to inhibit tissue ingrowth and endothelialization into the covering material.

7. The device of claim 1, wherein the covering material is attached to the stent frame.

8. The device of claim 1, wherein in the un-deployed configuration the free ends of the hook portions point radially outward.

* * * * *